United States Patent [19]

Patel

[11] Patent Number: 5,639,447
[45] Date of Patent: Jun. 17, 1997

[54] QUICK-DRYING NAIL POLISH

[75] Inventor: Mukesh Patel, Voorhees, N.J.

[73] Assignee: Mycone Dental Corporation, Cherry Hill, N.J.

[21] Appl. No.: 434,146

[22] Filed: May 2, 1995

[51] Int. Cl.$^6$ ................................................ A61K 7/04
[52] U.S. Cl. ................................... 424/61; 424/401
[58] Field of Search ................................. 424/401, 61

[56] References Cited

U.S. PATENT DOCUMENTS

| | | | |
|---|---|---|---|
| 3,928,113 | 12/1975 | Rosenberg | 156/344 |
| 4,126,675 | 11/1978 | Boulogne et al. | 424/61 |
| 4,260,701 | 4/1981 | Lee, Jr. | 525/303 |
| 4,301,046 | 11/1981 | Schlossman | 260/16 |
| 4,596,260 | 6/1986 | Giuliano | 132/73 |
| 4,683,007 | 7/1987 | Horowitz et al. | 106/308 |
| 4,798,720 | 1/1989 | Holder | 424/61 |
| 5,045,309 | 9/1991 | Dell'Aquila | 424/61 |
| 5,093,108 | 3/1992 | Pappas et al. | 424/61 |
| 5,098,696 | 3/1992 | Montgomery | 424/61 |
| 5,118,495 | 6/1992 | Nafziger et al. | 424/61 |
| 5,174,996 | 12/1992 | Weber et al. | 424/401 |
| 5,206,011 | 4/1993 | Pappas et al. | 424/61 |
| 5,275,807 | 1/1994 | Pappas et al. | 424/61 |
| 5,456,905 | 10/1995 | Valenty | 424/61 |
| B1 4,596,260 | 7/1988 | Giuliano | 132/88.5 |

*Primary Examiner*—Thurman K. Page
*Assistant Examiner*—Sharon Howard
*Attorney, Agent, or Firm*—Panitch Schwarze Jacobs & Nadel, P.C.

[57] ABSTRACT

Quick drying nail polish compositions for application to natural or artificial nails are provided. The quick-drying nail polish composition comprises a lacquer component and an optional pigment component. The lacquer component can dry in less than about 70 seconds in ambient atmosphere. The lacquer component includes benzophenone as a hardening accelerator.

22 Claims, No Drawings

QUICK-DRYING NAIL POLISH

FIELD OF THE INVENTION

The present invention relates to quick-drying nail polish compositions for application to natural or artificial fingernails or toenails in ambient atmospheres. The present invention also relates to methods for preparing quick drying nail polish compositions.

BACKGROUND OF THE INVENTION

Numerous types of liquid nail polish formulations are sold commercially. Liquid nail polish formulations typically contain a primary film former such as nitrocellulose, a secondary film former such as toluene-sulfonamide-formaldehyde resin, a plasticizer such as camphor or dibutyl phthalate, and one or more solvents such as toluol, lower aliphatic alcohols, and acetates. In addition, these formulations usually contain coloring agents and fragrances.

There are a number of desirable properties which nail polish compositions should possess. In particular, a nail polish should dry and harden quickly, apply easily, be adherent, glossy, waterproof and suitably colored, wear well, be elastic, resist chipping, peeling and abrasion for a reasonable period of time, and be dermatologically innocuous.

An important property of a nail polish is its ability to dry rapidly when applied to a natural human, or even in some instances, natural animal (such as dogs) or artificial fingernail or toe nail. In practice, this rapid-drying property is difficult to achieve while retaining the other desirable characteristics such as gloss, wear resistance, etc. The coating process, however, can be time consuming since a coating of polish must dry before a subsequent coating can be applied to the first coating. Since the average drying time for a coating of conventional nail polish is about five minutes, the total time for completing the nail polishing process using conventional compositions can be 15 minutes or more.

The time consuming aspects of applying nail polish is of particular concern to women who work outside the home. These women need to have a product which can be easily applied and which dries in the shortest amount of time. Also, in the manicure and pedicure industries such as nail care and beauty salons, a nail polish which can dry in a period less than one minute would provide a significant advantage over the prior art compositions.

The art has attempted to reduce the time required for drying of nail polishes. For example, U.S. Pat. No. 5,275,807 provides a number of solvent systems which may be added to standard nail polish formulations to substantially hasten drying of a nail enamel composition to a durable, hard finish. These solvent systems, however, use highly volatile and noxious acetone. A need therefore continues for nail polish formulations which can dry rapidly and which overcome the disadvantages of the art.

SUMMARY OF THE INVENTION

One aspect of the present invention relates to a nail polish composition which, when applied as a coating to natural or artificial nails, dries in time periods of less than about 70 seconds in ambient atmosphere. The quick-drying nail polish compositions of the invention comprise a lacquer component having about 5% to about 40% by weight primary film-forming polymer; about 1% to about 30% by weight secondary film-forming polymer; about 0.1% to about 6% by weight of at least one plasticizer; an amount of at least one thixotropic agent effective to gel said composition; about 8% to about 80% solvent system, and about 0.1% to about 1% drying accelerator, wherein the amounts are based on the total weight of the lacquer component.

In another aspect, the nail polish compositions may include a pigment component. The pigment component can comprise a pigment, a brightening agent, a primary film former, solvent, thixotropic agent, plasticizer and an aromatic ketone selected from the group consisting of 2,2-dimethoxy-2-phenyl acetophenone, 1-hydroxy cyclohexyl phenyl ketone, 2-hydroxy-2-methyl-1-phenyl-propane-1-one and 2,4,6-trimethyl benzoldiphenyl.

The nail polish compositions of the invention provide substantial advantages over the art. For example, the compositions of the invention dry in less than about 70 seconds without streaking or smudging. Other advantages will become apparent from the detailed description.

DETAILED DESCRIPTION OF THE INVENTION

The nail polish compositions of the invention can be formulated as a clear, colorless lacquer component, optionally mixed with a pigment component when a colored polish is desired. The lacquer component comprises a low boiling point solvent system, drying accelerator, primary and secondary film formers, as well as plasticizers and a thixotropic agent. The pigment component comprises pigments, a primary film former, a brightening agent, thixotropic agent, plasticizer, aromatic ketones, and solvents.

The lacquer component can include about 5% to about 40%, preferably about 12% to about 19%, more preferably about 7% to about 11% by weight, and most preferably about 5% of a primary film-forming polymer; about 1% to about 30%, preferably about 8% to about 18%, and most preferably about 12% by weight of a secondary film-forming polymer; about 0.1% to about 6%, preferably about 0.2% to about 0.5%, and most preferably about 0.3% by weight of at least one plasticizer; about 0.2% to about 0.4% of least one thixotropic agent effective to produce gelling of the lacquer component; about 8% to about 80% of a solvent system, preferably about 45% to about 55% solvent system; and about 0.1% to about 1%, preferably about 0.1% to about 0.4% drying accelerator, wherein the above percentages are based on the total weight of the lacquer component. The amount of secondary film-forming polymer in the lacquer component is effective to strengthen the primary film-forming polymer and to provide a film having an effective gloss and adhesion.

Primary film-forming polymers useful in the lacquer component include any of nitrocellulose, cellulose acetate-butyrate, especially nitrocellulose. The amounts of primary film former and secondary film former are chosen to produce a hardened coating thickness of about 0.0001 inch to 0.0005 inch, preferably about 0.0001 inch. Primary film-formers useful in the lacquer component are selected for their hardness, toughness, resistance to abrasion and ability to release solvent rapidly. Useful primary film formers include nitrocellulose, lower molecular weight resins such as RS nitrocellulose, acrylics such as ethyl methacrylate and phenolics such as toluene sulfamide resin, preferably nitrocellulose. Nitrocellulose may be employed in a concentration of about 70%, wet with about 30% ethanol or isopropanol.

Nitrocelluloses useful in the lacquer component are readily available commercially and have viscosity grades SS/2 or RS ¼ sec. The RS ¼ sec. grade has a high solids content. Other useful viscosity grades include RS ½ sec. which has a high non-volatile content, as well as the RS 5 sec., RS 6 sec., RS 60 sec., and the RS 80 sec. grades. RS nitrocellulose is presently preferred.

The term RS refers to the RS nitrocellulose that has a nitrogen content of about 11.2% to about 12.8% and is soluble in esters, ketones and glycol ethers. RS nitrocellulose is available from Hercules, Inc., Wilmington, Del., U.S.A., among other suppliers. The terms ¼ sec., ½ sec., 5 sec., etc. represent measurement of viscosity and refer to the time it takes for a ball to fall to a given depth in the material.

Secondary film formers useful in the lacquer component are chosen on the basis of their ability to build film and to enhance the depth, gloss and adhesion of the applied polish. Useful secondary film formers include but are not limited to celluloses such as ethyl cellulose, cellulose acetate, and cellulose acetate-butyrate; vinyl polymers such as polyvinyl acetate, and polyvinyl butyrate; ether urethanes such as polyurethane resins; and polyester resins formed from monomers ethyl acrylate and ethyl methylacrylate. Preferably, ethyl acrylate and/or ethyl methacrylate in an amount of about 7% to about 11% by weight of the lacquer component can be employed with benzoyl peroxide catalyst as the secondary film former. Other polyester resins which may be employed can be obtained from mixtures of 2,2,4-trimethyl-1,3-pentanediol, isophthalic acid-85, and trimellitic anhydride. The polyester resins can be formed by combining these constituents in the presence of a catalyst such as a dibutyl tin oxide by methods known in the art.

Solvent systems suitable for use in the lacquer component typically include ethyl acetate with at least one of isobutyl acetate and butyl acetate. High-boiling point solvents such as xylene and heptane may be added to the solvent system, but care must be taken to limit the use of such solvents to low levels to avoid increasing the drying time above acceptable limits. An acceptable drying time for the lacquer component is less than about 70 seconds.

Other useful solvent systems for use in the lacquer component include mixtures of lower alkyl acetates, lower alkyl alcohols, and lower alkyl ketones. Preferably, the solvent system includes about 5% to about 50%, preferably about 20% to about 45% ethyl acetate; about 3% to about 50%, preferably about 15% to about 35% isobutyl acetate or butyl acetate; up to about 20%, preferably about 0.2% to about 11% isopropanol or ethanol; and about 0.5% to about 30%, preferably about 10% to about 20% methylethyl ketone, based on the weight of the solvent system.

Plasticizers employed in the lacquer component are chosen to impart flexibility to the hardened nail coating. The choice of plasticizer may vary as a function of the color, odor, effect on viscosity of the enamel, effect on the drying rate, the amount needed to meet flexibility requirements, the volatility of the plasticizer, as well as compatibility with the other components of the compositions.

Plasticizers which may be used in the lacquer component include dibutyl phthalate, butyl phthalate, butyl glycolate, triphenyl phosphate, tricresyl phosphate, diamylphthalate, dibutyl phthalate, diethyl phthalate, dibutoxy ethyl phthalate, dioctyl phthalate, castor oil, benzyl benzoate, tributyl phosphate, butyl acetyl ricinoleate, butyl stearate, triethyl citrate, dibutyl tartrate and diamyl phthalate. Preferably, dibutyl phthalate is employed in the lacquer component in an amount of about 0.1% to about 0.98, preferably about 0.28 to about 0.5%, most preferably about 0.3% by weight of the lacquer component.

Drying accelerators for use in the lacquer component are effective to cause the lacquer composition to dry in an ambient atmosphere in less than about 70 seconds. Useful drying accelerators include benzophenone and benzoyl peroxide in amounts of about 0.1% to about 1%, preferably about 0.1% to about 0.4%, most preferably about 0.4% by weight of the lacquer component.

The lacquer component employed in the invention also includes a thixotropic agent in an amount effective to gel the composition. Useful thixotropic agents include stearalkonium hectorites such as Bentone™ 27, Bentone™ 28, especially Bentone™ 27. Typically, the thixotropic agent is present in an amount of about 0.18 to about 5%. Preferably, the lacquer component includes about 0.28 to about 0.3% Bentone™ 27 based on the weight of the lacquer component. Bentones™ are available from NL Industries, N.J., U.S.A.

In another aspect of the invention, a pigment component can be mixed with the lacquer component to provide colored, rapid drying nail polish compositions. The amount of pigment component may be about 0.5% to about 50%, typically about 0.5% to about 35% based on the combined weight of the lacquer component and the pigment component.

The pigment component comprises pigment, brightening agent, plasticizer, primary film former, optional secondary film former, thixotropic agent, solvent and aromatic ketone. Choice of pigment is based on the desired color of the polish. Useful pigments include but are not limited to D & C Red #6, #7, #9, #10, #30, #33 and #34 Lakes, D & C Yellow #5 Lakes, titanium dioxide, mica, iron oxides, iron black aluminum silicate and iron blue aluminum silicate. In addition to the above-named pigments irridescent additives such as "pearl essence" which is a suspension of crystalline guanine in nitrocellulose and solvents may be employed. Especially useful pigments include D & C pigments, titanium dioxide, and mica. The amount of pigment in the pigment component may be about 1% to about 85%, preferably about 30% to about 45% of the pigment component.

Useful brightening agents include bismuth oxychloride, hydrated alumina and preferably bismuth oxychloride in an amount of about 1% to about 18%, preferably about 2% to about 8%, most preferably about 4% to about 5% of the total weight of the pigment component.

Plasticizers which may be used in the pigment component include camphor, dibutyl phthalate and preferably camphor, in an amount of about 0.1% to about 6%, preferably about 0.8% to about 1%, based on the total weight of the pigment component.

The thixotropic agent included in the pigment component enhances suspension of pigment and the other components of the pigment component composition. Although a number of thixotropic agents may be employed in the pigment component, preferred thixotropic agents include thixotropic clays, preferably stearalkonium hectorites such as the Bentones™, more preferably Bentone 27™. The amount of thixotropic agent in the pigment component may be about 0.1% to about 5%, preferably about 0.2% to about 2%, and more preferably about 0.3% to about 0.9% of the total weight pigment component, depending on the nature and type of pigment and other ingredients forming the pigment component.

The primary film former employed in the pigment component is believed to function as a binder for the pigment employed in the pigment component. Useful primary film formers include nitrocelluloses such as those mentioned above for use in the lacquer component. The primary film former can be combined with optional secondary film former polymers such as those employed in the lacquer component. Nitrocellulose, however, is preferably employed alone. The amount of nitrocellulose employed in the pigment component may be about 5% to about 40%, preferably about 2% to about 18%, most preferably about 16% of the total weight of the pigment component.

Solvents useful in the pigment component include lower alkyl acetates, preferably isobutyl acetate and ethyl acetate, in amounts of about 1% to about 50%, preferably about 30% to about 45% of the total weight of the pigment component. Other useful solvents include butyl acetate.

Exemplary aromatic ketones useful in the pigment component include 2,2-dimethoxy-2-phenyl acetophenone, 1-hydroxy cyclohexyl phenyl ketone, 2-hydroxy-2-methyl-1-phenyl-propane-1-one and 2,4,6-trimethyl benzoldiphenyl. The aromatic ketones may comprise about 0.01% to about 1% of the total weight of pigment component. Preferably, the aromatic ketone is 2-hydroxy-2-methyl-1-phenyl-propane-1-one in an amount of about 0.2% to about 0.3% of the pigment component.

In formulating the lacquer component, solvents are mixed to produce a low boiling point solvent system. Thereafter, a primary film-forming polymer, a secondary film-forming polymer and at least one plasticizer are added step-wise in any order in conjunction with vigorous mixing until a viscous solution is produced. After the viscous solution is produced, a thixotropic agent is added to the solution in conjunction with vigorous stirring for a period sufficient to produce the lacquer component.

In formulating the pigment component, a thixotropic agent is added to a solvent. Thereafter, the primary film former and the optional secondary film formers are added, followed by plasticizer. Pigments and aromatic ketones then are added.

In formulating pigmented nail polish compositions, the pigment component is added to the lacquer component. The pigment component is added to the lacquer component to constitute about 0.5% to about 50%, preferably about 0.5% to about 35% of the pigmented nail polish composition. The rate of addition of the pigment component to the lacquer component may vary over wide limits. Preferably the pigment component is added batch-wise to the lacquer component to provide a mixture. The mixture then is subjected to mixing at about 180 rpm to about 250 rpm for about 20 to about 30 minutes in a cowles mixer. The resulting average particle size of the pigment component typically is about 1 to about 8 microns. Preferably, the average particle size is the finest grind on the Gardner Grind Gauge (Hegman Gauge).

The nail polish compositions of the present invention, with or without the pigment component, have characteristics of quick-drying, flexibility, durability, adequate viscosity and high gloss. The nail polish compositions of the invention "dry" in a period of less than about 60 to about 80 seconds, preferably less than about 70 seconds. As used herein, "dry" is understood to mean that the compositions, when applied to a human or artificial nail, do not evidence tack (absence of smudging) after about 60 to about 80 seconds at room temperature and at a relative humidity of about 50%.

The composition of the invention are durable and typically do not chip or crack for a period of at least about three days of wearing on a human or synthetic nail. Coatings formed of the lacquer component per se, as well as the coatings formed from compositions which include both the lacquer and pigment components, exhibit an acceptable gloss.

The viscosities of the nail polish compositions of the invention, with or without the pigment component are commercially acceptable. The static viscosities of the nail polish compositions of the invention are about 180 centipoise to about 480 centipoise, preferably about 250 centipoise. Static viscosities can be determined by Brookfield viscometer. In addition to static viscosities, the shaken viscosities of the compositions of the invention are also commercially acceptable.

Each of the lacquer and pigment components, as well as mixtures of the lacquer and pigment components, are storage stable and may be applied to a human or artificial nail even after extended storage. There is no need to include, for example, a steel ball to enable a vigorous shaking of the composition before application as is required by many of the compositions of the prior art.

In order to evaluate the quick drying nail polish compositions prepared according to the invention, a series of nail polishes are prepared as described above and tested for drying times in Examples 1–4 below. Generally, in Examples 1–4, the lacquer component is produced by adding nitrocellulose, commercial grade ethyl methacrylate and dibutyl phthalate stepwise to a solvent system formed of ethyl acetate, isobutyl acetate, isopropyl alcohol, and methyl ethyl ketone by vigorous mixing until a viscous solution is produced. After the viscous solution is produced, Bentone™ 27 thixotropic agent is added to the solution in conjunction with vigorous stirring for a period sufficient to produce a gelled lacquer component.

The pigment component employed in Examples 1–4 below is formulated by adding Bentone™ 27 to isobutyl acetate or ethyl acetate. Thereafter, nitrocellulose is added, followed by camphor. Pigments and aromatic ketones then are added.

The present invention will now be described in more detail with reference to the following specific, non-limiting examples.

EXAMPLES 1–4

In Examples 1–4, the nail polishes are prepared from various lacquer components and pigment components as described above. The lacquer component employed has one of the following exemplary compositions A-1, A-2 or A-3:

| LACQUER COMPONENT COMPOSITION | A-1 | A-2 | A-3 |
|---|---|---|---|
| Ethyl Acetate | 40.3% | 35.0% | 32.0% |
| Isobutyl Acetate | 21.3 | 24.1 | 25.0 |
| Isopropyl Alcohol | 6.0 | 6.5 | 6.0 |
| Methyl Ethyl Ketone | 11.5 | 13.5 | 16.1 |
| Nitrocellulose | 15.0 | 14.7 | 14.6 |
| Commercial Grade Ethyl Methacrylate | 5.0 | 5.2 | 5.2 |
| Dibutyl Phthalate | 0.3 | 0.4 | 0.5 |
| Benzophenone | 0.4 | 0.3 | 0.4 |
| Bentone ™27 | 0.2 | 0.3 | 0.2 |
| Fragrance (trace) | | | |

The pigment component employed in the examples below has one of the following exemplary compositions B-1 or B-2:

| PIGMENT COMPONENT COMPOSITION | B-1 | PIGMENT COMPONENT COMPOSITION | B-2 |
|---|---|---|---|
| Bismuth Oxychloride | 4.5% | Bismuth Oxychloride | 4.0% |
| D & C #7 Pigment | 28.0 | D & C #6 Pigment | 15.0 |

-continued

| PIGMENT COMPONENT COMPOSITION | B-1 | PIGMENT COMPONENT COMPOSITION | B-2 |
|---|---|---|---|
| Blue D & C Iron Oxide | 0.7 | D & C #7 Pigment | 10.0 |
| Titanium Dioxide | 5.6 | Titanium Dioxide | 1.5 |
| 2-hydroxy-2-methyl-1-phenyl-propane-1-one | 0.2 | Yellow #5 | 20.5 |
| Camphor | 1.0 | 2-hydroxy-2-methyl-1-phenyl-propane-1-one | 0.3 |
| Nitrocellulose | 14.0 | Camphor | 1.0 |
| Bentone ™27 | 0.3 | Nitrocellulose | 14.5 |
| Isobutyl Acetate | 45.7 | Ethyl Acetate | 32.3 |
|  |  | Bentone ™27 | 0.9 |

The nail polishes are applied to human finger nails as a thin film of about 0.0001 inch thick. The films of nail polish are determined to be dry when they no longer smudge upon touching. The amount of time required for each film to dry is recorded. The compositions of the lacquer and pigment components, as well as the drying times of nail polishes produced from these components, are given in Table I.

TABLE I

| Example No. | Lacquer Component Composition (%)[1] | Pigment Component Composition (%)[1] | Drying Time[2] (Seconds) |
|---|---|---|---|
| 1 | A1-93% | B1-7% | 69 |
| 2 | A1-90% | B2-10% | 62 |
| 3 | A2-95% | B1-5% | 68 |
| 4 | A3-88% | B2-12% | 61 |

[1]Based on combined weights of the lacquer and pigment components.
[2]Measured on 0.0001 inch film thickness at 77° F.

The present invention may be embodied in other specific forms without departing from the spirit or essential attributes thereof and, accordingly, reference should be made to the appended claims, rather than to the foregoing specification as indicating the scope of the invention.

What is claimed is:

1. A quick-drying nail polish composition having the property of drying in less than about 70 seconds in ambient atmosphere, said composition having a lacquer component comprising
   (a) about 5% to about 40% by weight primary film-forming polymer;
   (b) about 1% to about 30% by weight secondary film-forming polymer;
   (c) about 0.1% to about 6% by weight of at least one plasticizer;
   (d) an amount of at least one thixotropic agent effective to gel said composition;
   (e) about 8% to about 80% by weight solvent system, and
   (f) about 0.1% to about 1% by weight drying accelerator selected from the group consisting of benzophenone and benzoyl peroxide,
   said amounts based on total weight of the lacquer component.

2. The composition according to claim 1 wherein said primary film-forming polymer is a nitrocellulose.

3. The composition according to claim 2 wherein the nitrocellulose is RS nitrocellulose.

4. The composition according to claim 1 wherein said secondary film-forming polymer is selected from the group consisting of cellulose acetate, cellulose acetate-butyrate, ethyl cellulose, polyvinyl acetate, and polyvinyl butyrate.

5. The composition according to claim 4 wherein said plasticizer is selected form the group consisting of dibutyl phthalate, camphor and mixtures thereof.

6. The composition according to claim 5 wherein said plasticizer is dibutyl phthalate.

7. The composition according to claim 6 wherein said primary film-forming polymer is nitrocellulose;
   said secondary film-forming polymer is polyester resin formed from monomer selected from the group consisting of ethyl acrylate and ethyl methacrylate and mixtures thereof; and
   said solvent system comprises ethyl acetate, at least one of isobutyl acetate and butyl acetate, at least one of isopropanol and ethanol, and methylethyl ketone.

8. The composition of claim 7 wherein, based on the weight of the solvent system, said ethyl acetate is present in said solvent system an amount of about 5% to about 50%,
   said at least one of isobutyl acetate and butyl acetate is present in said solvent system an amount of about 3% to about 50%,
   said at least one of isopropanol and ethanol is present in said solvent system an amount of up to about 20%, and
   said methylethyl ketone is present in said solvent system an amount of about 0.5% to about 30%.

9. The composition of claim 8 wherein said dibutyl phthalate is present in an amount of about 0.1% to about 0.9%.

10. The composition of claim 9 wherein said secondary film former is present in an amount of about 7% to about 11%.

11. The composition of claim 10 wherein said primary film former is present in an amount of about 12% to about 19%.

12. The composition of claim 1 wherein the thixotropic agent is present in an amount of about 0.1% to about 5%.

13. A quick-drying nail polish composition comprising the lacquer component of claim 1 and a pigment component, said composition having ability to dry in a period of less than about 70 seconds in ambient atmosphere,
   said pigment component comprising a pigment, a brightening agent, a primary film former, solvent, thixotropic agent, plasticizer and an aromatic ketone selected from the group Consisting of 2,2-dimethoxy-2-phenyl acetophenone, 1-hydroxy cyclohexyl phenyl ketone, 2-hydroxy-2-methyl-1-phenyl-propane-1-one and 2,4,6-trimethyl benzoldiphenyl.

14. The composition of claim 13 wherein said pigment is present in an amount of about 1% to about 85% based on total weight of said pigment component.

15. The composition according to claim 14 wherein said primary film-forming polymer is nitrocellulose,
   said solvent is selected from the group consisting of isobutyl acetate and ethyl acetate, and
   said plasticizer is camphor.

16. The composition of claim 15 wherein said solvent is present in an amount of about 1% to about 50% based on total weight of said pigment component.

17. The composition of claim 16 wherein said primary film former is nitrocellulose present in an amount of about 5% to about 40% of said pigment component based on total weight of said pigment component.

18. The composition of claim 17 wherein said plasticizer is camphor present in an amount of about 0.2% to about 6% of said pigment component based on total weight of said pigment component.

19. The composition of claim 13 wherein said brightening agent is present in an amount of about 1% to about 18%.

20. The composition of claim 13 wherein said thixotropic agent in the pigment component is present in an amount of about 0.2% to about 2%.

21. A composition for coating natural and synthetic nails of animals and humans, said composition capable of drying in an ambient atmosphere in less than about 70 seconds, said composition comprising a lacquer component and a pigment component, said pigment component being present in an amount of about 0.5% to about 35% based on the weight of said composition, remainder lacquer component,
  (a) said lacquer component comprising, based on total weight of said lacquer component,
    about 45% to about 55% of a solvent system comprising ethyl acetate, and an acetate selected from the group consisting of i-butyl acetate and butyl acetate, an alcohol selected from the group of i-propanol and ethanol, and methylethyl ketone,
    about 12% to about 19% nitrocellulose,
    about 7% to about 11% of at least one of ethyl acrylate and ethyl methacrylate,
    about 0.2% to about 0.5% dibutyl phthalate,
    about 0.3% to about 0.4% stearalkonium hectorite and
    about 0.1% to about 0.4% benzophenone; and
  (b) said pigment component comprising, based on total weight of said pigment component,
    about 2% to about 8% bismuth oxychloride,
    about 30% to about 45% pigment,
    about 0.8% to about 1% camphor,
    about 0.2% to about 2% stearalkonium hectorite,
    about 30% to about 45% of an acetate selected from the group consisting of isobutyl acetate and ethyl acetate, and
    about 0.2% to about 0.3% aromatic ketone.

22. A quick-drying nail polish composition having the property of drying in less than about 70 seconds in ambient atmosphere, said composition having a lacquer component comprising
  (a) about 5% to about 40% by weight primary film-forming polymer;
  (b) about 1% to about 30% by weight secondary film-forming polymer;
  (c) about 0.1% to about 6% by weight of at least one plasticizer;
  (d) an amount of at least one thixotropic agent effective to gel said composition;
  (e) about 8% to about 80% by weight solvent system, and
  (f) about 0.1% to about 1% by weight drying accelerator;
  said amounts (a), (b), (c) (d) (e) and (f) based on total weight of the lacquer component;
  said composition having a pigment component comprising
  (g) about 1% to about 85% by weight pigment;
  (h) a brightening agent;
  (i) about 5% to about 40% by weight primary film former, said primary film former being nitrocellulose;
  (j) about 1% to about 50% by weight solvent selected from the group consisting of isobutyl acetate and ethyl acetate;
  (k) a thixotropic agent;
  (l) about 0.2% to about 6% by weight plasticizer, said plasticizer being camphor; and,
  (m) about 0.01% to about 1% by weight of an aromatic ketone, said aromatic ketone being 2-hydroxy-2-methyl-1-phenyl-propane-1-one;
  said amounts (g), (h), (i), (j), (k), (l) and (m) based on total weight of the pigment component.

* * * * *